(12) United States Patent
Schule

(10) Patent No.: US 9,149,657 B2
(45) Date of Patent: Oct. 6, 2015

(54) WATER PHANTOM AND MEASUREMENT SYSTEM

(75) Inventor: Edmund Schule, March (DE)

(73) Assignee: PTW-Freiburg Physikalisch-Technische Werkstätten Dr. Pychlua GmbH, Freiburg (DE)

( * ) Notice: Subject to any disclaimer, the term of this patent is extended or adjusted under 35 U.S.C. 154(b) by 468 days.

(21) Appl. No.: 13/616,518

(22) Filed: Sep. 14, 2012

(65) Prior Publication Data

US 2013/0068939 A1 Mar. 21, 2013

(30) Foreign Application Priority Data

Sep. 16, 2011 (DE) .......................... 10 2011 113 611

(51) Int. Cl.
*G01D 18/00* (2006.01)
*A61N 5/10* (2006.01)
(52) U.S. Cl.
CPC ....... *A61N 5/1075* (2013.01); *A61N 2005/1076* (2013.01)
(58) Field of Classification Search
CPC .................... A61N 2005/1076; A61N 5/1075; G01T 1/02
USPC .............. 250/252.1, 374, 375, 389, 362, 363; 356/139.03; 324/318; 33/503; 378/23, 378/11, 12, 205, 207, 208; 382/132; 700/98; 600/424
See application file for complete search history.

(56) References Cited

U.S. PATENT DOCUMENTS

| | | | | |
|---|---|---|---|---|
| 3,864,568 A * | 2/1975 | Helgesson | .................. | 250/252.1 |
| 5,621,214 A * | 4/1997 | Sofield | .......................... | 250/375 |
| 5,635,709 A * | 6/1997 | Sliski et al. | ................ | 250/252.1 |
| 6,207,952 B1 * | 3/2001 | Kan et al. | .................... | 250/252.1 |
| 6,225,622 B1 * | 5/2001 | Navarro | ...................... | 250/252.1 |
| 7,073,271 B2 * | 7/2006 | Raab et al. | ...................... | 33/503 |
| 7,147,373 B2 * | 12/2006 | Cho et al. | ....................... | 378/207 |
| 7,174,651 B2 * | 2/2007 | Raab et al. | ...................... | 33/503 |
| 7,193,220 B1 * | 3/2007 | Navarro | ....................... | 250/374 |
| 7,382,129 B2 * | 6/2008 | Mills | ............................. | 324/318 |
| 7,420,160 B2 * | 9/2008 | Delaperriere et al. | ..... | 250/252.1 |
| 7,605,365 B2 * | 10/2009 | Chen et al. | ................. | 250/252.1 |
| 7,614,157 B2 * | 11/2009 | Granger | .......................... | 33/503 |
| 8,183,522 B2 * | 5/2012 | Celi de la Torre et al. | | 250/252.1 |

(Continued)

FOREIGN PATENT DOCUMENTS

DE 3725760 2/1989
DE 102005030648 4/2007

(Continued)

*Primary Examiner* — Kiho Kim
(74) *Attorney, Agent, or Firm* — Volpe and Koenig, P.C.

(57) ABSTRACT

A measurement system for use in radiation therapy, for example for measuring radiation sources, in particular for a water phantom. The water phantom has a water container and a measurement system, on which at least one holder for a radiation detector is arranged. The holder can be moved within the water container along at least one movement axis, with a control unit being present, which accepts and executes commands for controlling the movement axis. A virtual coordinate system which is aligned to the water surface is defined so that the movement device does not have to be aligned with great complexity. A conversion unit transfers control commands from the virtual coordinate system into the real coordinate system of the movement device so movements of the holder are always parallel and/or perpendicular to the water surface.

12 Claims, 2 Drawing Sheets

(56) References Cited

U.S. PATENT DOCUMENTS

| | | | |
|---|---|---|---|
| 8,321,179 B2 * | 11/2012 | Simon et al. | 702/189 |
| 2003/0080297 A1 * | 5/2003 | Bales et al. | 250/353 |
| 2005/0151963 A1 * | 7/2005 | Pulla et al. | 356/139.03 |
| 2008/0048125 A1 * | 2/2008 | Navarro | 250/389 |
| 2008/0075227 A1 * | 3/2008 | Christoph et al. | 378/23 |
| 2008/0144913 A1 * | 6/2008 | Yoshida | 382/132 |
| 2008/0236260 A1 * | 10/2008 | Noda et al. | 73/105 |
| 2010/0176284 A1 * | 7/2010 | Navarro | 250/252.1 |
| 2010/0243875 A1 * | 9/2010 | Plompen et al. | 250/252.1 |
| 2011/0022360 A1 * | 1/2011 | Simon et al. | 702/189 |
| 2011/0052036 A1 * | 3/2011 | Valdivieso Cacique et al. | 382/132 |
| 2011/0278444 A1 * | 11/2011 | Navarro | 250/252.1 |
| 2013/0068939 A1 * | 3/2013 | Schule | 250/252.1 |
| 2013/0334426 A1 * | 12/2013 | Freimann | 250/362 |
| 2014/0148690 A1 * | 5/2014 | Kim et al. | 600/424 |
| 2014/0371895 A1 * | 12/2014 | Sadusk et al. | 700/98 |

FOREIGN PATENT DOCUMENTS

| | | |
|---|---|---|
| EP | 1923000 | 5/2008 |
| GB | 649704 | 1/1951 |
| JP | 2011133467 | 7/2011 |

* cited by examiner

WATER PHANTOM AND MEASUREMENT SYSTEM

CROSS-REFERENCE TO RELATED APPLICATIONS

This application claims the benefit of German Patent Application No. 102011113611.1, filed Sep. 16, 2011, which is incorporated herein by reference as if fully set forth.

BACKGROUND

The invention describes a measurement system, in particular for a water phantom, with at least one movement axis on which at least one holder for a radiation detector is arranged, wherein the holder can be moved along at least one movement axis, wherein a control unit is present, which accepts and executes commands for controlling the movement axis.

By way of example, such a measurement system is used in a water phantom in radiation therapy within the scope of quality control or commissioning of irradiation devices, such as accelerators. Here, the radiation field of the irradiation device is measured with the aid of a radiation detector, which is for example moved in a water container which is filled with water (a so-called water phantom).

The water in the water phantom has a specific absorption rate for radiation which approximately corresponds to that of human tissue. So that, for example, a measurement of the two-dimensional distribution is meaningful, it is decisive that the absorption is the same at all measurement points of the measurement plane. This is achieved by virtue of the water level above the detector always remaining constant.

In the process, the coordinate system in which the radiation detector is moved is generally defined by the mechanical movement axes, along which the movement takes place in one, two or three spatial dimensions. The mechanical movement axes must therefore be aligned precisely with respect to the water surface of the water phantom so that the water level is exactly equal at various positions of a measurement plane.

Adjusting the movement axes by hand or using an electric motor is the current prior art. In one embodiment, the movement axes are fixedly assembled on the water container. Now the whole unit, including water container and movement axes, is aligned horizontally and therefore parallel to the water surface. In another embodiment, the movement axes are attached on the water container in adjustable fashion and can be horizontally aligned independently of the latter. Here, there is no need to align the water container as long as all that is demanded is a parallel alignment with the water surface, but not, at the same time, a parallel alignment with the walls of the water container.

After the alignment, a movement along the fixed movement axes is always parallel or perpendicular to the water surface.

However, this mechanical alignment of the movement device with respect to the water surface requires much care and is very time-consuming. Moreover, the movement device must have additional means for the alignment, as a result of which the device is more complicated and expensive.

SUMMARY

It is therefore an object of the invention to develop a water phantom, the design of which is simpler and more convenient. This object is achieved by a measurement system with one or more features of the invention.

Instead of the mechanical adjustment of the movement axes there is a coordinate transformation into a virtual coordinate system which is aligned with respect to the water surface. The movement then takes place with transformed coordinates in the real coordinate system of the movement axes, which need not be aligned.

In order to compensate for possible angled positions of the movement axes, and hence of the real coordinate system, an rZ movement axis necessarily has to be present.

As a result of the coordinate transformation, a one-dimensional movement in the virtual coordinate system may, in certain circumstances, require a two-dimensional or even three-dimensional movement in the real coordinate system.

The advantage of the measurement system according to the invention now is provided in the fact that a time-consuming adjustment and alignment of the movement device with respect to the reference plane is no longer required.

Moreover, the movement device need not be designed for aligning and is therefore simpler and more cost-effective.

The virtual coordinate system is aligned with respect to the reference plane. Here the virtual coordinate axes, depending on number of and desired movement direction(s), are respectively aligned parallel and/or perpendicular to the reference plane.

Movements are then defined in the virtual coordinate system. The conversion unit transforms these movements into the real coordinate system and transmits the new movement commands to the control unit, which actuates the movement axes in a known manner.

Since the measurement system with the fixedly connected movement axes can have a different angled position with respect to a reference plane during each use, the virtual coordinate system must initially be aligned with respect to the reference plane.

This can occur in many different ways. By way of example, the position of the movement axes with respect to the reference plane can be determined by manual or automatic adjustment.

It is particularly advantageous if a measurement device is present, which enables an automated or automatic determination of the virtual coordinate system. Hence there is no need for manual intervention in the system and the adjustment is simple, reliable and precise.

In one advantageous embodiment, the measurement device has at least one sensor for determining the distance from the reference plane. In order to set the virtual coordinate system, the distance from the reference plane is determined at at least two measurement points and the angle of the angled position is determined therefrom. A rotation matrix and the virtual coordinate system can be derived from the angle of the angled position.

Alternatively, use can also be made of other sensors or measurement concepts for determining the angle of the angled position with respect to the reference plane.

By way of example, the distance can be determined by tactile sensors, by means of ultrasound or by means of a laser.

By way of example, a distance sensor may be present for determining an angle, said distance sensor being arranged on the movement device such that various measurement points can be approached.

Alternatively, the measurement device can preferably have at least two distance sensors, which are arranged at a defined distance from one another in the real coordinate system.

By way of example, a plane on a radiation source which lies perpendicular to the radiation direction can serve as a reference plane. However, the reference plane can also be a surface of a solid or liquid absorber, which can be arranged in the beam path between the measurement system and a radiation source.

In particular, the reference plane can be the water surface of a water phantom. Here, the distance sensors can be water sensors, for example.

The movement device expediently has an electric motor as a drive for each movement axis. Here, the electric motors can, for example, be configured as stepper motors.

In order to actuate the movement axes, a control unit is present, the latter for example having a microcontroller or microprocessor.

The conversion unit is expediently realized together with the control unit in a microcontroller.

BRIEF DESCRIPTION OF THE DRAWINGS

In the following text, the invention is explained in more detail with reference to the attached drawings using the example of a water phantom.

Shown in detail are.

DETAILED DESCRIPTION OF THE PREFERRED EMBODIMENTS

Figure 1:
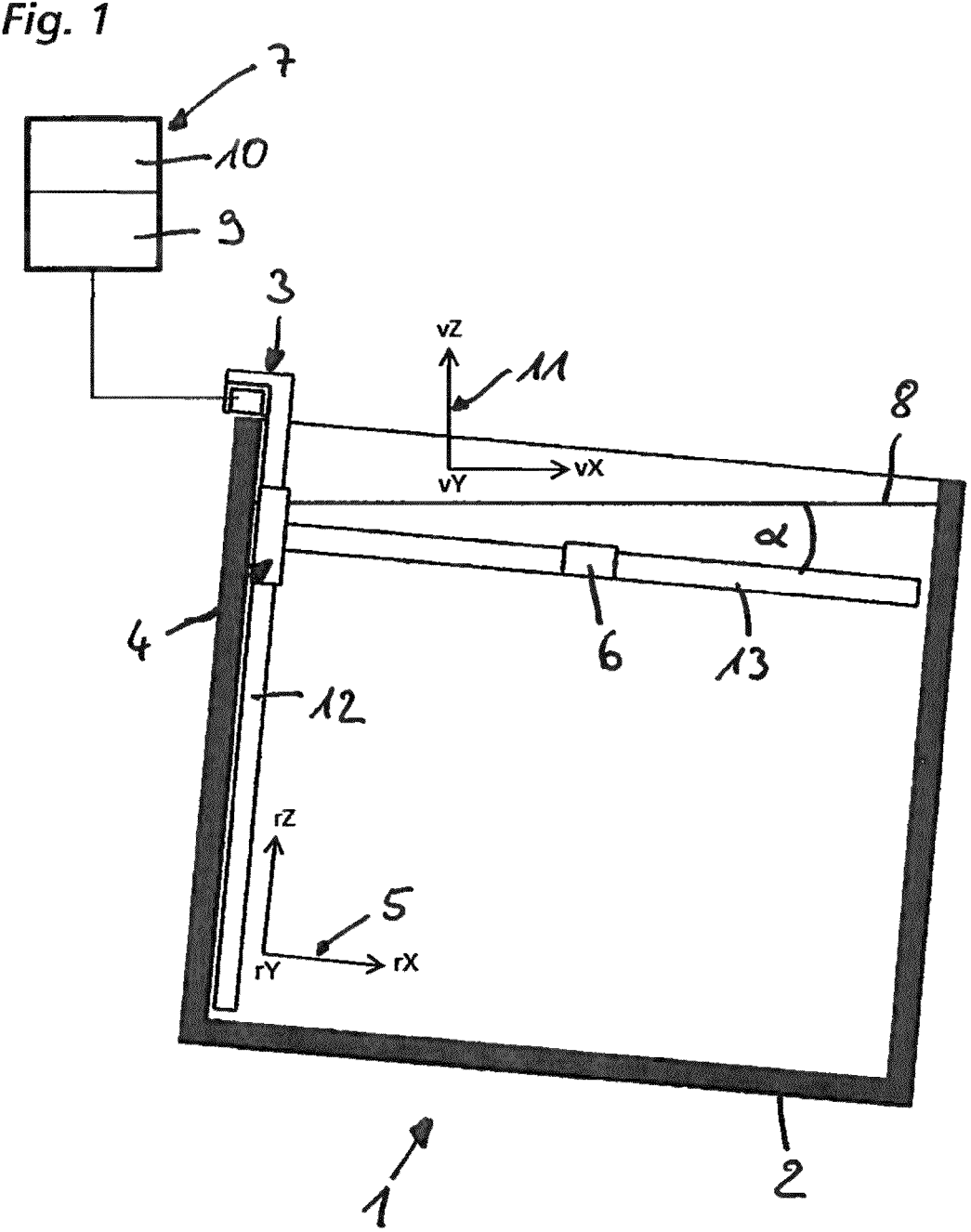
FIG. 1 is a view of a water phantom with a measurement system according to the invention at an angled position.

FIG. 1 shows a water phantom 1 with a water container 2 and a measurement system 3 attached thereon. In the example, the measurement system 3 has three movement axes 4, which define a real coordinate system 5 with coordinate axes rN (N=X, Y, Z). Furthermore, a holder 6 is situated on the rX movement axis 13 of the measurement system 3, to which e.g. a radiation detector (not illustrated) can be attached. As a result, the radiation detector can be positioned within the water container 2 in order, for example, to measure the two-dimensional or three-dimensional distribution of the radiation intensity of a radiation source.

By way of example, the movement axes 4 have electric motors, by which a movement can be controlled in a very precise manner. In order to actuate the electric motors, the phantom 1 has a control unit 9, which accepts and converts movement commands. By way of example, the movement commands can contain absolute or relative coordinates or paths on the movement axes 4. The control unit 9 is preferably realized in a microcontroller 7 or microprocessor, which contains the control unit 9 as an operating program.

In the image, the water container 1 is tilted about the rY coordinate axis of the real coordinate system 5, and so the real rX coordinate axis is not aligned parallel to the water surface 8 and the rZ coordinate axis is not aligned perpendicular thereto. The rY coordinate axis is perpendicular to the plane of the paper and therefore cannot be illustrated.

In the case of a movement of the holder 6 along the rX movement axis 13, the distance of the holder 6 from the water surface 8 therefore necessarily changes, as a result of which the absorption rate is modified. As a result, it is not possible to undertake a meaningful radiation measurement along the rX movement axis 13.

A virtual coordinate system 11 is therefore defined in the water phantom 1 according to the invention, the virtual coordinate axes vN (N=X, Y, Z) of which are aligned with respect to the water surface 8 as reference plane. That is to say the virtual coordinate axes vN are arranged parallel and perpendicular to the water surface 8.

The water phantom 1 has a conversion unit 10, which converts movement commands in the virtual coordinate system 11 into movement commands in the real coordinate system 5 and transmits these to the control unit 9.

The conversion unit 10 practically carries out a coordinate transformation from the virtual coordinate system 11 into the real coordinate system 5. The conversion unit 10 is expediently realized together with the control unit in the operating program of the microcontroller 7.

As a result of this, it is now possible for all movement commands to be specified in the virtual coordinate system 11 such that the movements are always aligned with respect to the water surface 8. The conversion unit 10 transforms the movement commands into the real coordinate system 5 in a completely transparent manner, and so the movement axes 4 are actuated accordingly.

In the process, a movement along a movement axis in the virtual coordinate system 11 can, depending on the tilt of the water container, by all means lead to a three-dimensional movement of the holder 6 in the real coordinate system 5.

In order to compensate for angled positions of the water container 2, the movement device 3 requires, as a matter of principle, a movement axis 12 in the rZ direction.

So that the coordinate transformation is possible, the virtual coordinate system 11 must be known or firstly be determined. This is expediently carried out in an automatic or automated fashion.

Figure 2:
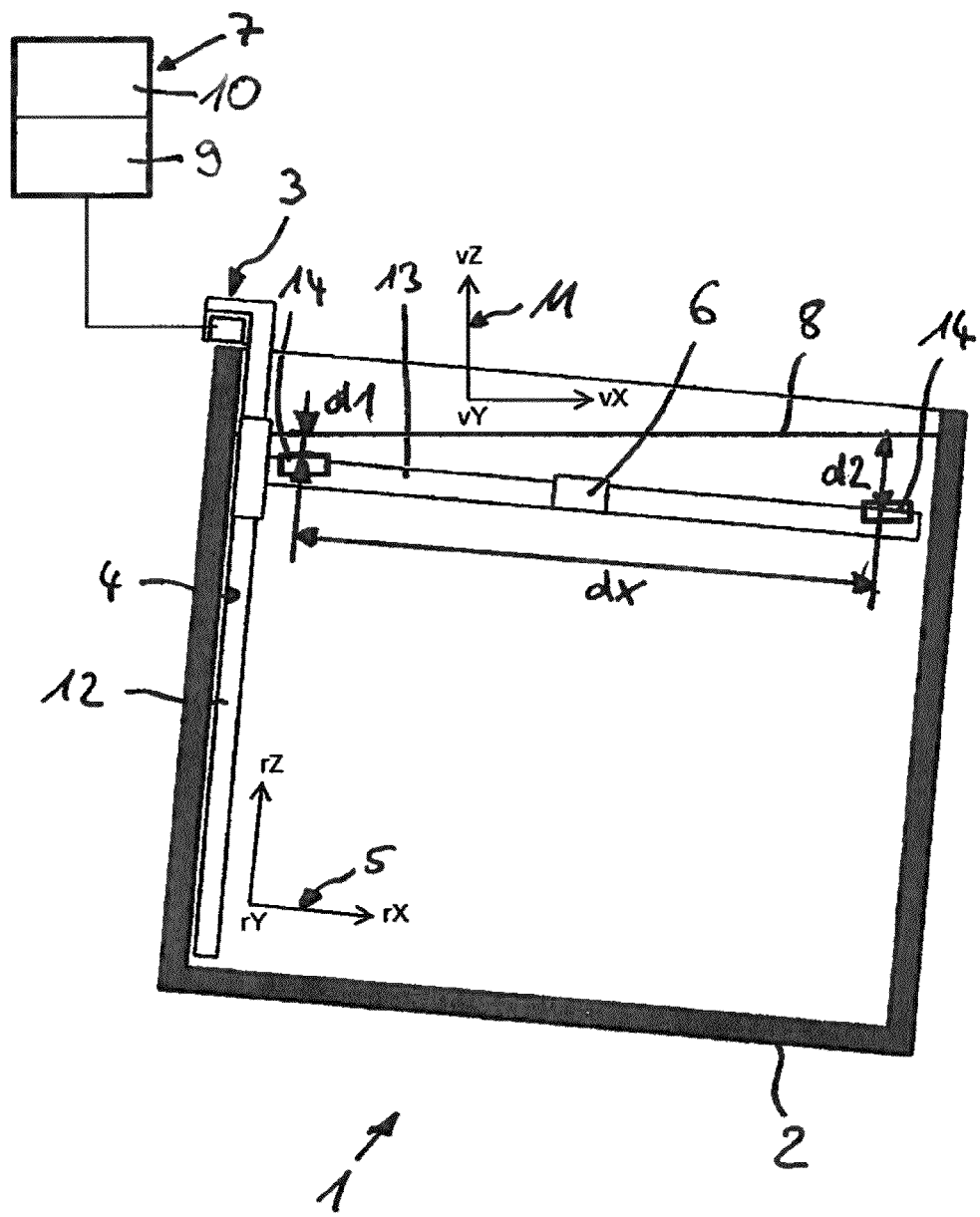
FIG. 2 shows a water phantom according to the invention with two distance sensors respectively arranged at the ends of a movement axis.

FIG. 2 shows, in an exemplary fashion, an arrangement by which an automatic determination of the virtual coordinate system 11 is possible. To this end, two water or distance sensors 14 are arranged at the ends of the rX movement axis 13. By way of example, such a water sensor 14 can have a float, which keeps a switching contact open under water and closes the latter outside of the water. However, it is also possible to use other mechanical or electric water or distance sensors.

In order to measure the distance from the water surface, the rX movement axis 13 is in this case moved in the rZ direction, for example from the base or a fixed position upward, until both sensors 14 have emerged from the water. From the distance dx between the sensors 14 in the real coordinate system 5 and the measured distances d1, d2 of the sensors 14 from the water surface 8 it is possible to determine the angle of rotation α as per $$\tan\alpha = \frac{d2-d1}{dx}.$$

Alternatively, d2−d1=dy can also be determined directly by virtue of only starting a distance measurement when the first sensor 14 has emerged from the water and completing it when the second sensor 14 has emerged.

Using the angle of rotation α it is possible to generate a rotation matrix in a known fashion; the latter serves to transform the coordinates from the virtual coordinate system 11 into the real coordinate system 5.

A possible tilt about the rX coordinate axis can be determined by a further distance sensor in the rY direction.

The virtual coordinate system is preferably determined by a program which runs in the microcontroller 7.

Automated determination of the virtual coordinate system 11 is also possible without fixedly installed water sensors 14.

To this end, a water sensor 14 is for example arranged on the holder 6 in place of a radiation detector.

Then the sensor is respectively used to measure the distance from the water surface 8 at various fixedly predetermined measurement points in the real coordinate system 5.

Depending on the number of movement axes, two or at most three measurement points suffice for this. From the established distances in the real coordinate system, it is possible to determine the angle or angles of rotation about which the water container is rotated using the aforementioned equation. From this, it is possible to generate a rotation matrix for the coordinate transformation.

The automated or automatic determination of the virtual coordinate system 11 only requires little time and little or no intervention by the user and is therefore substantially simpler, faster and more accurate than the mechanical alignment of the movement axes.

However, the invention is not restricted to the application in a water phantom. By way of example, a solid-state absorber may be arranged in the beam path instead of the water, without changing the measurement principle. Then the reference plane is not the water surface but a surface of the solid-state absorber. The virtual coordinate system is then determined analogously by measuring the distances from this surface.

The invention can also be used entirely without absorbers. To this end, a reference plane can be arranged with respect to the radiation source or freely in space, which plane is aligned perpendicularly to the radiation direction. Here the virtual coordinate system is also determined by measuring the distance between movement axes and reference plane at a plurality of measurement points. In this case, the distance can for example be measured by ultrasound or a laser.

LIST OF REFERENCE SIGNS

1 Water phantom
2 Water container
3 Measurement system
4 Movement axis
5 Real coordinate system
6 Holder
7 Microcontroller
8 Water surface
9 Control unit
10 Conversion unit
11 Virtual coordinate system
12 rZ movement axis
13 rX movement axis
14 Water sensor
rX, rY, rZ Real coordinate axes
vX, vY, vZ Virtual coordinate axes
α Angle of rotation
d1, d2 Distances from the water surface
dx Distance between water sensors

The invention claimed is:

1. A measurement system for a water phantom, comprising at least one movement axis on which at least one holder for a radiation detector is arranged, the holder is movable along the movement axis, a control unit which accepts and executes commands for controlling the movement axes, a real coordinate system is present, the real coordinate axes of which are respectively defined by the movement axes, a virtual coordinate system is present, the virtual coordinate axes of which are aligned with respect to a reference plane, and a conversion unit is configured to convert movement commands in the virtual coordinate system into movement commands in the real coordinate system and transmits the movement commands in the real coordinate system to the control unit such that a movement of the holder always takes place at least one of parallel or perpendicular to the reference plane and the measurement system has at least an rZ movement axis, and a measurement device that enables an automated or automatic determination of the virtual coordinate system, the measurement device has at least one water sensor for determining a distance from the reference plane defined by a water surface.

2. The measurement system as claimed in claim 1, wherein the distance from the reference plane is determined at two or more measurement points for setting the virtual coordinate system.

3. The measurement system as claimed in claim 1, wherein the measurement device has at least two of the water sensors for determining the distance to the water surface, which are arranged at defined distances from one another in the real coordinate system.

4. The measurement system as claimed in claim 1, wherein the water sensor for determining the distance to the water surface is arranged on the at least one holder on the movement device, by which various measurement points can be approached.

5. The measurement system as claimed in claim 1, wherein the movement device has an electric motor as a drive for each of the movement axes.

6. The measurement system as claimed in claim 1, wherein the conversion unit and the control unit are realized in a microcontroller.

7. The measurement system as claimed in claim 1, wherein the reference plane is arranged on a radiation source.

8. A water phantom with a water container and a measurement system as claimed in claim 1, in which the rZ movement axis is aligned perpendicularly to a floor of the water container.

9. The water phantom as claimed in claim 8, wherein the reference plane is a water surface is of a water container which is filled with water.

10. A method for carrying out a measurement of radiation intensity using a water phantom, comprising: determining a distance from a reference plane defined by a water surface using at least one water sensor, determining a virtual coordinate system, with the virtual coordinate axes being aligned with respect to the water surface, prior to each movement of a movement axis, converting movement commands for the measurements in the virtual coordinate system into movement commands in a real coordinate system of the movement axes, and carrying out the movement of the movement axes with the coordinates in the real coordinate system.

11. The method as claimed in claim 10, wherein, in order to determine the virtual coordinate system, the method further comprises measuring the distance to the water surface at two or more predefined measurement points of the real coordinate system and calculating at least one of an angle of rotation or a rotation matrix therefrom.

12. The method as claimed in claim 10, wherein a coordinate transformation is undertaken with the aid of a rotation matrix in order to convert the coordinates.

* * * * *